US012569117B2

(12) United States Patent
Ashizuka et al.

(10) Patent No.: US 12,569,117 B2
(45) Date of Patent: Mar. 10, 2026

(54) ENDOSCOPE

(71) Applicant: OLYMPUS MEDICAL SYSTEMS CORP., Tokyo (JP)

(72) Inventors: Masahiro Ashizuka, Hino (JP);
Takuya Toyooka, Hachioji (JP)

(73) Assignee: Olympus Medical Systems Corp.,
Tokyo (JP)

( * ) Notice: Subject to any disclaimer, the term of this
patent is extended or adjusted under 35
U.S.C. 154(b) by 405 days.

(21) Appl. No.: 18/116,339

(22) Filed: Mar. 2, 2023

(65) Prior Publication Data

US 2023/0277039 A1    Sep. 7, 2023

Related U.S. Application Data

(60) Provisional application No. 63/316,049, filed on Mar. 3, 2022.

(51) Int. Cl.
*A61B 1/00*        (2006.01)
*A61B 1/018*       (2006.01)

(52) U.S. Cl.
CPC ...... *A61B 1/00094* (2013.01); *A61B 1/00114* (2013.01); *A61B 1/018* (2013.01)

(58) Field of Classification Search
CPC ............ A61B 1/00094; A61B 1/00–32; A61B
1/00114; A61B 1/018; A61B 1/00071;
A61B 1/00066; A61B 1/0052; A61B
1/00098; A61B 2017/0034; G02B
23/2423; G02B 23/24; A61M 1/918;
A61M 25/0029
USPC ................... 600/132, 156, 104, 109; 606/46
See application file for complete search history.

(56) References Cited

U.S. PATENT DOCUMENTS

| | | | | |
|---|---|---|---|---|
| 5,573,494 | A | * 11/1996 | Yabe | ................... A61B 1/0051 |
| | | | | 600/106 |
| 2003/0187460 | A1 | * 10/2003 | Chin | ................. A61B 17/3421 |
| | | | | 606/129 |
| 2008/0214890 | A1 | 9/2008 | Motai et al. | |
| 2008/0214895 | A1 | * 9/2008 | Campos | ................ A61B 1/307 |
| | | | | 600/129 |
| 2016/0316998 | A1 | * 11/2016 | Lombardi | .............. A61B 1/307 |

(Continued)

FOREIGN PATENT DOCUMENTS

| | | | |
|---|---|---|---|
| JP | H04-279141 A | 10/1992 | |
| JP | H07-194525 A | 8/1995 | |

(Continued)

*Primary Examiner* — Anh T Nguyen
*Assistant Examiner* — James Edward Boice
(74) *Attorney, Agent, or Firm* — Morgan, Lewis & Bockius LLP

(57)        ABSTRACT

An endoscope including an insertion portion including a distal end structure and an active bending section, an image sensor located in the distal end structure, and the image sensor has an optical axis in a first direction, and the first direction intersects a central longitudinal axis of the distal end structure, a treatment instrument channel located in the distal end structure and adjacent the image sensor, and a distal end opening of the treatment instrument channel opens in a second direction, and the second direction intersects the central longitudinal axis, and a suction channel located in the distal end structure, wherein a distal end opening of the suction channel opens in a third direction, and the third direction is different from the second direction.

13 Claims, 6 Drawing Sheets

(56)             References Cited

U.S. PATENT DOCUMENTS

| | | | |
|---|---|---|---|
| 2016/0367233 A1* | 12/2016 | Mamiya | A61B 1/05 |
| 2020/0196843 A1* | 6/2020 | Tah | A61B 1/00094 |
| 2020/0246531 A1* | 8/2020 | Lenihan | A61M 1/3659 |
| 2021/0076909 A1* | 3/2021 | Ueda | A61B 1/0014 |
| 2022/0039643 A1* | 2/2022 | Barnes | A61B 1/125 |
| 2023/0225591 A1* | 7/2023 | Ji | A61B 1/00128 |
| | | | 600/136 |
| 2024/0298878 A1* | 9/2024 | Miller | A61B 1/00137 |

FOREIGN PATENT DOCUMENTS

| | | | |
|---|---|---|---|
| JP | 2003-033315 A | 2/2003 |
| JP | 2003-038426 A | 2/2003 |
| JP | 2004-267596 A | 9/2004 |
| JP | 2008-212671 A | 9/2008 |

* cited by examiner

ENDOSCOPE

CROSS-REFERENCE TO RELATED APPLICATION

This application is based on and claims priority under 35 U.S.C. § 119 to U.S. Provisional Application No. 63/316, 049, filed on Mar. 3, 2022, the entire contents of which are incorporated herein by reference.

FIELD OF THE DISCLOSURE

The present disclosure relates to an endoscope in which a treatment instrument channel and a suction channel are separately provided.

BACKGROUND

Conventionally, an endoscope has widely been used in, for example, a medical field and an industrial field. In general, the endoscope is configured to include an elongated tube-shaped insertion portion and a distal end portion provided at a distal end of the insertion portion. Such endoscopes include a front-viewing endoscope, a side-viewing endoscope, and the like.

In such a side-viewing endoscope, a treatment instrument inserted into a treatment instrument insertion channel is caused to change a projecting direction by a treatment instrument raising base (forceps elevator) provided in a distal end portion of an insertion portion of the endoscope and projects through an opening provided on a side surface of the distal end portion of the insertion portion of the endoscope.

The treatment instrument insertion channel of the endoscope can be used as a conduit for suction as well as for insertion of the treatment instrument, and can draw out fluid, such as body fluid, through a treatment instrument projecting hole of the treatment instrument insertion channel.

SUMMARY

An endoscope, comprising: insertion portion including a distal end structure and an active bending section; an image sensor located in the distal end structure, wherein the image sensor has an optical axis in a first direction, and the first direction intersects a central longitudinal axis of the distal end structure; a treatment instrument channel located in the distal end structure and adjacent the image sensor, wherein a distal end opening of the treatment instrument channel opens in a second direction, and the second direction intersects the central longitudinal axis; and a suction channel located in the distal end structure, wherein a distal end opening of the suction channel opens in a third direction, and the third direction is different from the second direction.

DETAILED DESCRIPTION

In general, in a case where a treatment instrument insertion channel is used as a conduit for suction, the body fluid occasionally adheres to the inside of the treatment instrument insertion channel. Therefore, in a case where after an insertion portion of the endoscope is inserted to a portion to be treated, a treatment instrument is inserted into the treatment instrument insertion channel, there is a risk that bacteria adhere to the treatment instrument via the body fluid adhering to the inside the treatment instrument insertion channel.

According to the embodiments described below, an endoscope capable of reducing the risk of adhesion of bacteria to the treatment instrument inserted into the treatment instrument insertion channel can be provided.

Hereinafter, the embodiments will be described in detail with reference to the drawings.

Note that the drawings based on the embodiments are schematic, and the relation between the thickness and the width of each portion, the ratios in thickness and the relative angles among the portions, and the like are different from the actual relation, ratios in thickness, relative angles, and the like. Some portions having relations and ratios in dimensions differing among the drawings are also included.

First Embodiment

Figure 1:
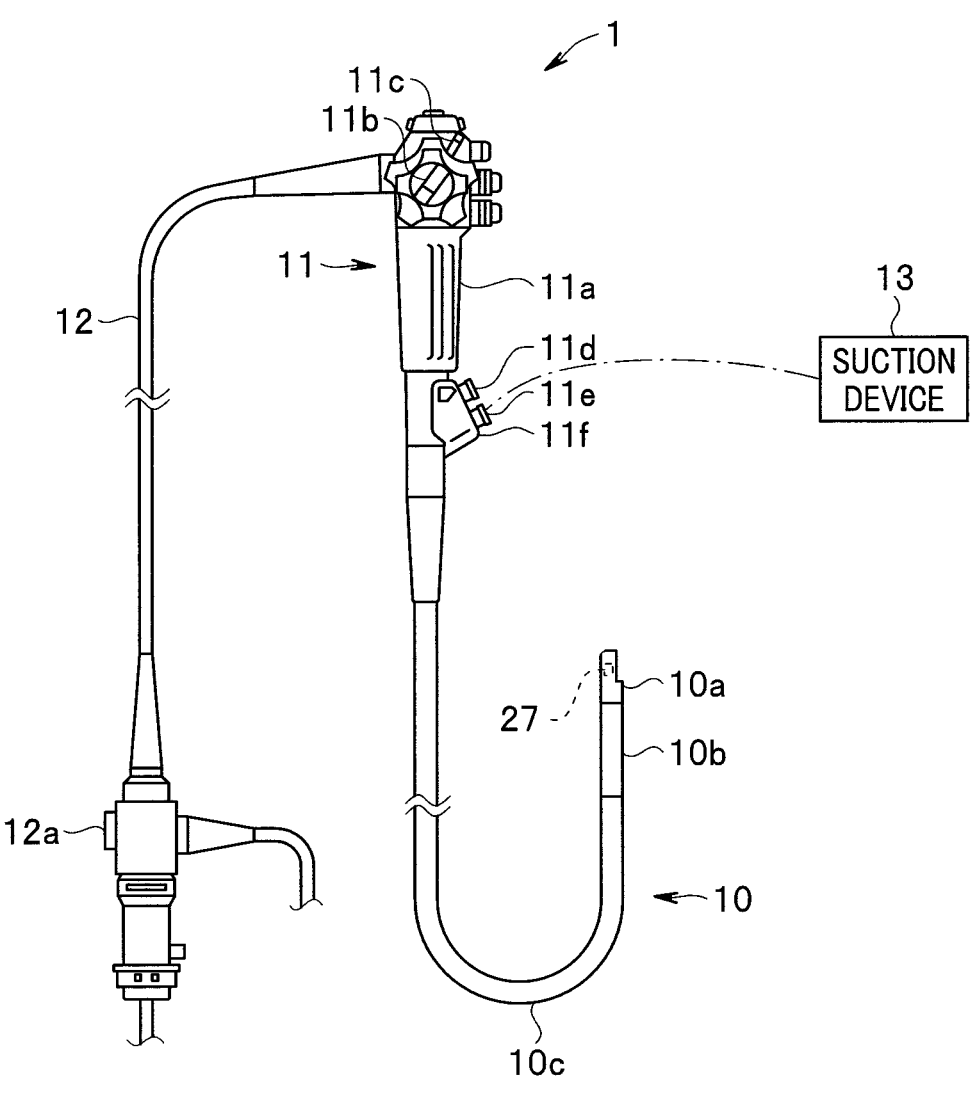
FIG. 1 is a view showing an example of the overall configuration of an endoscope according to a first embodiment.
Figure 2:
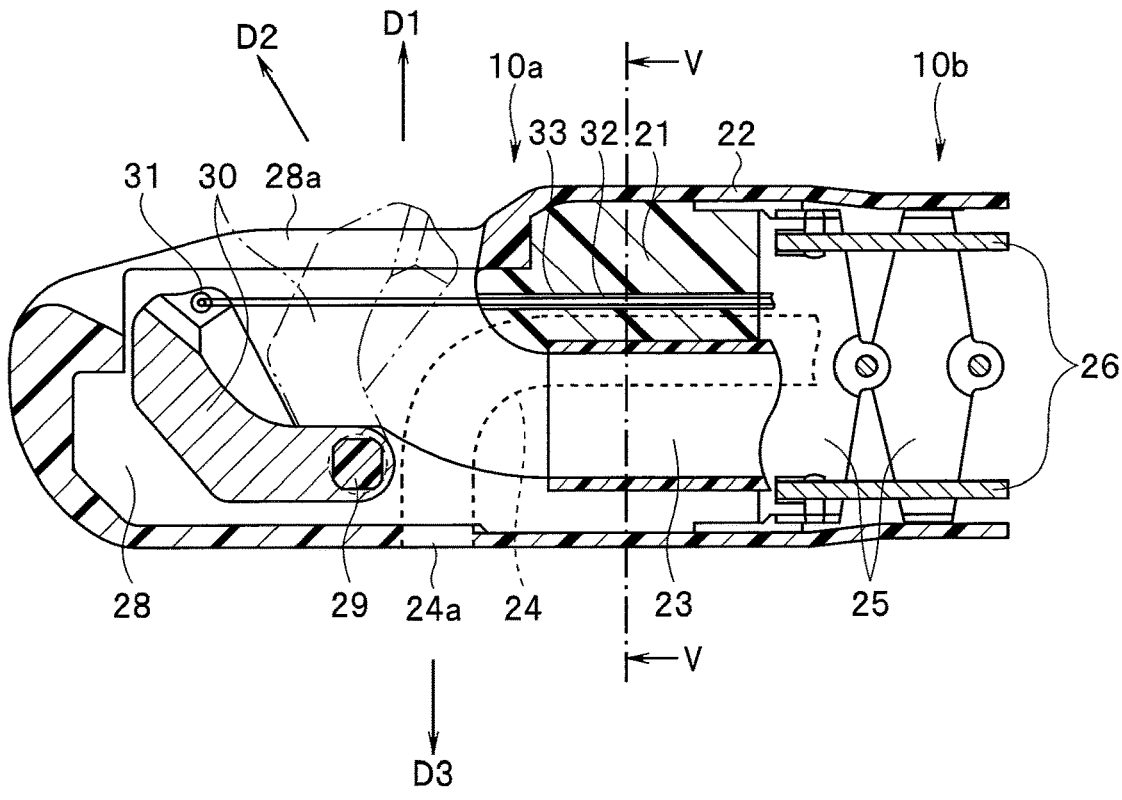
FIG. 2 is a cross-sectional view showing a configuration example in which a distal end structural portion of the endoscope is provided with a treatment instrument raising base that changes a direction in which a treatment instrument projects from a treatment instrument channel.
Figure 3:
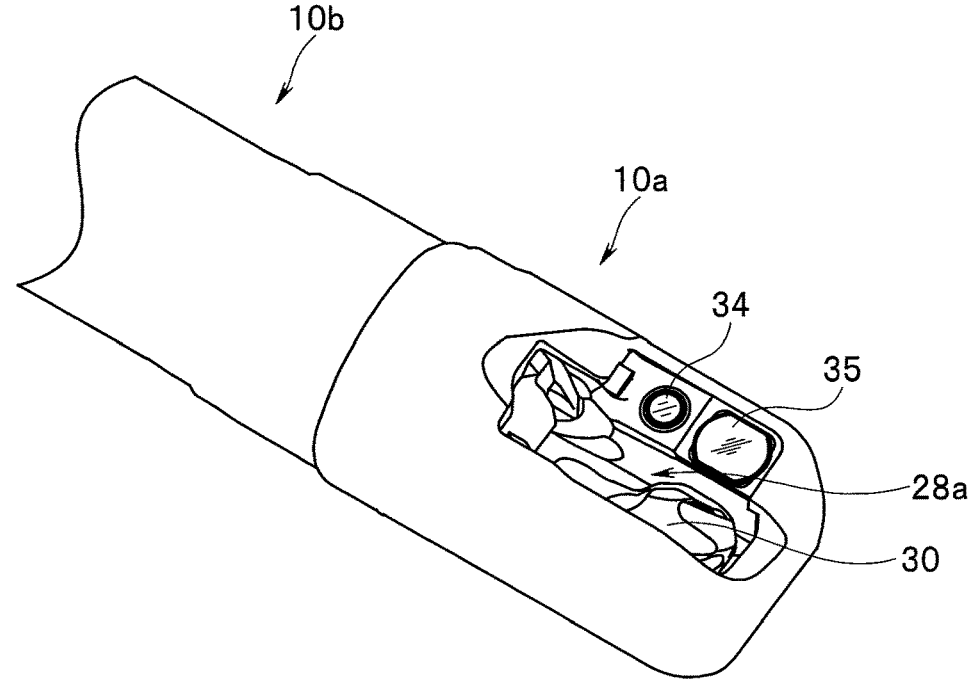
FIG. 3 is a perspective view showing the configuration of a distal end of an insertion portion of the endoscope according to the first embodiment.

FIG. 1 is a view showing an example of the overall configuration of an endoscope according to a first embodiment. FIG. 2 is a cross-sectional view showing a configuration example in which a distal end structural portion of the endoscope is provided with a treatment instrument raising base that changes a direction in which a treatment instrument projects from a treatment instrument channel. FIG. 3 is a perspective view showing the configuration of a distal end of an insertion portion of the endoscope according to the first embodiment.

As shown in FIG. 1, an endoscope 1 includes an insertion portion 10, an operation unit 11, and a universal cable 12.

The insertion portion 10 is an elongated site to be inserted into a body cavity of a subject. Note that the subject into which the insertion portion 10 is inserted is presumed to be a human body as an example, but is not limited to the human body and may be a living being such as an animal or an inanimate object such as a machine or a building.

The insertion portion 10 includes a distal end structural portion 10*a*, an active bending portion 10*b*, and a flexible tube portion 10*c* in the order from the distal end side toward the proximal end side. In the distal end structural portion 10*a*, an image pickup unit 27 for picking up an image of a subject is disposed.

As shown in FIG. 2, the distal end structural portion 10*a* is provided with a distal end portion main body 21, and an outer side of internal components of the insertion portion 10 including the distal end portion main body 21 is provided with a tubular exterior member 22. The inside of the exterior member 22 and the distal end portion main body 21 is configured as a lumen, and houses various internal components such as a treatment instrument channel 23, a suction channel 24, a bending piece 25, a bending wire 26, an image pickup unit 27 (see FIG. 1 and FIG. 5), a light guide 36 (see FIG. 5) that illuminates a subject, and an air and water feeding channel 37 (see FIG. 5) for feeding air and water.

The image pickup unit 27 is disposed in the distal end structural portion 10*a* of the insertion portion 10 and has an optical axis in a first direction D1 crossing the longitudinal axis of the insertion portion 10.

Figure 5:
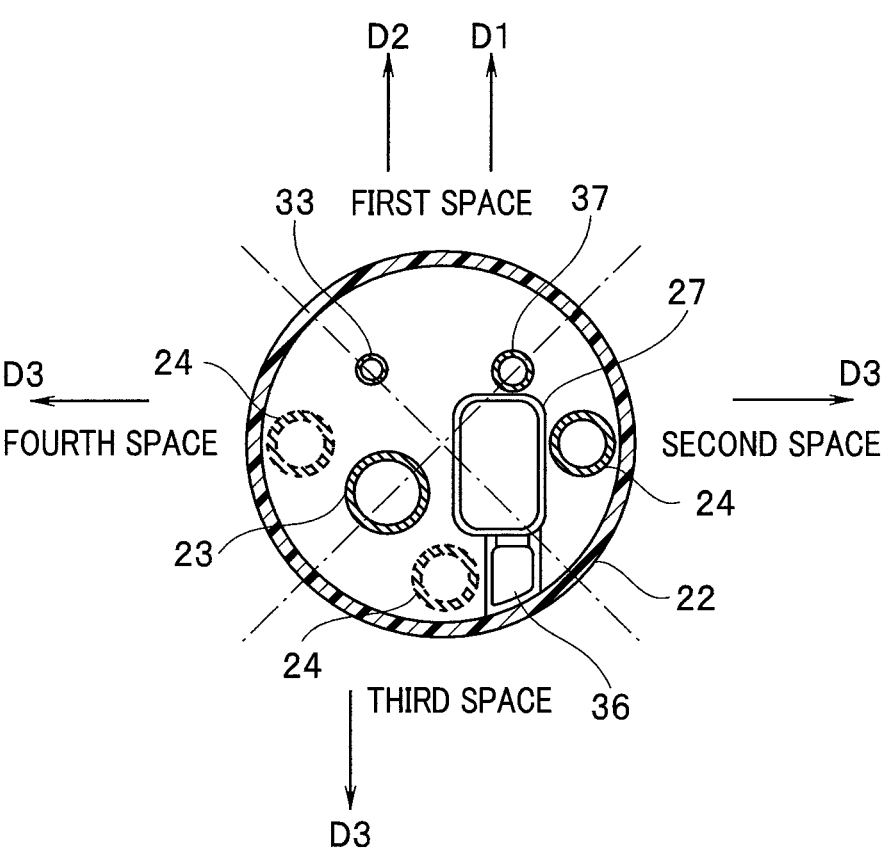
FIG. 5 is a cross-sectional view taken along line V-V of the distal end structural portion of FIG. 2.

The inside of the distal end structural portion 10*a* is provided with a housing chamber 28 communicating with the treatment instrument channel 23. The treatment instrument channel 23 may be a channel dedicated to a treatment instrument. The housing chamber 28 includes an opening 28*a* on one side surface of the distal end structural portion 10*a*. The opening 28*a* forms an opening portion communicating with the distal end of the treatment instrument channel 23. The treatment instrument channel 23 is provided adjoining to the image pickup unit 27 as shown in FIG. 5. In the distal end structural portion 10*a*, the treatment instrument channel 23 opens in a second direction D2 crossing the longitudinal axis of the insertion portion 10.

On a side surface opposite to the one side surface of the distal end structural portion 10*a* where the opening 28*a* is provided, an opening 24*a* as an opening portion communicating with the distal end of the suction channel 24 is provided. In this manner, in the distal end structural portion 10*a*, the suction channel 24 opens in a third direction D3 different from the second direction D2. The suction channel 24 may be a channel dedicated to suctioning.

Inside the housing chamber 28, a treatment instrument raising base 30 turnably supported by a support shaft 29 is disposed. The treatment instrument raising base 30 includes a connecting portion 31 to which one end of a raising wire 32 is connected. The raising wire 32 is inserted through a raising wire channel 33 and the other end is connected to a raising base operation knob 11*c*. An operator operates the raising base operation knob 11*c* to pull the raising wire 32 so that the treatment instrument raising base 30 turns from a stand-by position denoted by a solid line to a raised position denoted by a dashed-two dotted line.

In a state in which the treatment instrument projecting from the treatment instrument channel 23 is disposed on the treatment instrument raising base 30, the treatment instrument raising base 30 is turned to the raised position. As a result, the distal end portion of the treatment instrument, such as forceps, is raised and projects through the opening 28*a*.

As shown in FIG. 3, the distal end structural portion 10*a* includes an observation window (objective lens) 34 and an illumination lens 35 that adjoin the opening 28*a* of the treatment instrument channel 23. The image pickup unit 27 picks up an image of an observation site on the opening 28*a* side of the treatment instrument channel 23 via the observation window 34. The illumination lens 35 irradiates the opening 28*a* side of the treatment instrument channel 23 with an illumination light from the light guide 36.

The active bending portion 10*b* is a bendable site disposed on the proximal end side of the distal end structural portion 10*a*. The active bending portion 10*b* is configured to be bendable in, for example, two directions or four directions of upward, downward, leftward, and rightward.

Inside the active bending portion 10*b*, as shown in FIG. 2, a plurality of bending pieces 25 are continuously provided in a swingable manner along the longitudinal axis of the insertion portion 10, and the bending wire 26 is connected to the bending pieces 25 at the distal end. The proximal end of the bending wire 26 is connected to the bending operation knob 11*b* of the operation unit 11.

When the active bending portion 10*b* is bent, the direction of the distal end structural portion 10*a* changes, and an observing direction by the image pickup unit 27 and the irradiating direction of the illumination light from the light guide 36 change. The active bending portion 10*b* is also bent for the purpose of improving the insertability of the insertion portion 10 inside a subject.

The flexible tube portion 10*c* is a flexible tube portion that is disposed on the proximal end side of the active bending portion 10*b*.

The operation unit 11 is disposed on the proximal end side of the insertion portion 10 and includes a grasping portion 11*a*, the bending operation knob 11*b*, the raising base operation knob 11*c*, a treatment instrument insertion opening 11*d*, and a suction port 11*e*. The grasping portion 11*a* is a site with which an operator grasps the endoscope 1 by hand. The bending operation knob 11*b* is an operating device for performing operation of bending the active bending portion 10*b* by using a thumb, for example, of a hand grasping the grasping portion 11*a*. When the bending operation knob 11*b* is operated, the bending wire 26 is pulled so that the active bending portion 10*b* is bent.

The raising base operation knob 11*c* is an operating device for performing operation of raising the treatment instrument raising base 30 by using a thumb, for example, of a hand grasping the grasping portion 11*a*. When the raising base operation knob 11*c* is operated, the raising wire 32 is pulled so that the treatment instrument raising base 30 is raised. The operation unit 11 is also provided with various buttons for operating the endoscope 1.

In a predetermined position of the grasping portion 11*a*, a substantially triangular raised portion 11*f* is formed. The treatment instrument insertion opening 11*d* and the suction port 11*e* are provided in different positions on the same surface of the raised portion 11*f*. The suction port 11*e* is disposed on the insertion portion 10 side relative to the treatment instrument insertion opening 11*d*. The treatment instrument insertion opening 11*d* is an opening communicating with the proximal end of the treatment instrument channel 23 and for insertion of the treatment instrument into the treatment instrument channel 23. The treatment instrument insertion opening 11*d*, the treatment instrument channel 23, and the opening 28*a* communicate with one another as one conduit and do not merge with another conduit.

The suction port 11*e* is an opening provided in a position different from the treatment instrument insertion opening 11*d* and communicating with the proximal end of the suction channel 24 and for drawing out liquid such as body fluid. A suction device 13 is connected to the suction port 11*e* to draw out body fluid or the like.

Figure 4:
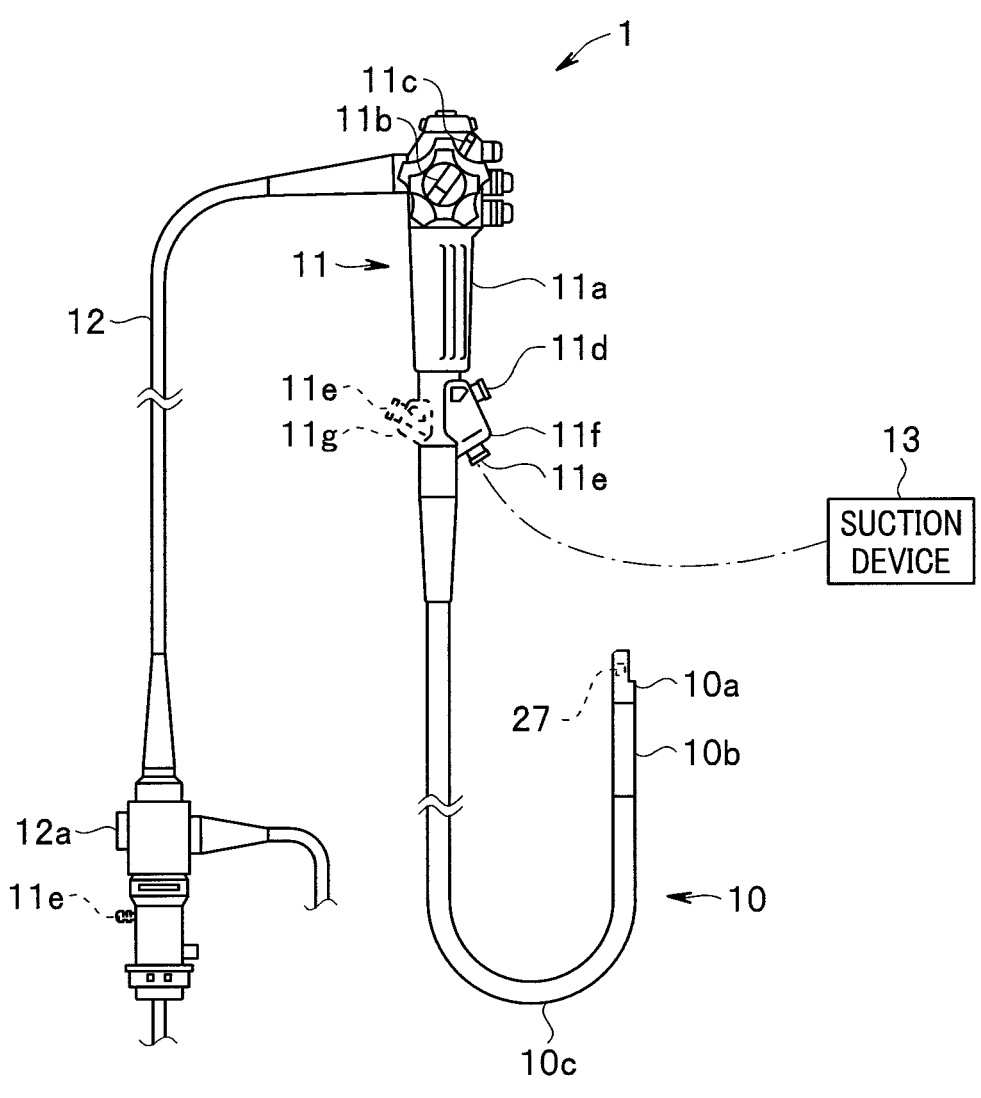
FIG. 4 is a view for explaining another example of a position where a suction port is provided.

Note that the position where the suction port 11*e* is provided is not limited to the position shown in FIG. 1, but may be another position. FIG. 4 is a view for explaining another example of the position where the suction port is provided. For example, as shown in FIG. 4, the suction port 11*e* may be provided on a surface different from the surface of the raised portion 11*f* where the treatment instrument insertion opening 11*d* is provided. As denoted by a sparse broken line of FIG. 4, the suction port 11*e* may be provided in a raised portion 11*g* formed on a second surface different from a first surface where the raised portion 11*f* of the grasping portion 11*a* is formed. Further, the suction port 11*e* may be provided in a connector 12*a*, which will be described later. In any case, the suction port 11*e*, the suction channel 24, and the opening 24*a* communicate with one another as one conduit and do not merge with another conduit.

The universal cable 12 extends from, for example, a side surface on the proximal end side of the operation unit 11 and an extension end is provided with the connector 12*a* for connection to a light source device and an endoscope control device.

Note that the position where the opening 24*a* of the suction channel 24 is disposed is not limited to the position shown in FIG. 2. For example, the opening 24*a* may be provided on the distal end side relative to the position where the opening 28*a* of the treatment instrument channel 23 is disposed. The opening 24*a* may be provided at the most distal end of the distal end structural portion 10*a*. In other words, the opening 24*a* may be provided in the longitudinal axis direction of the insertion portion 10. With the opening 24*a* provided on the distal end side relative to the opening 28*a* and the optical axis of the image pickup unit 27, the risk of liquid such as body fluid entering the treatment instrument channel 23 can be reduced.

The suction channel 24 may be disposed as shown in FIG. 5. FIG. 5 is a cross-sectional view taken along line V-V of the distal end structural portion of FIG. 2.

As shown in FIG. 5, the longitudinal axis of the insertion portion 10 is divided, in the circumferential direction, into first, second, third, and fourth spaces by 90 degrees. In this case, the first direction D1 as the optical axis of the image pickup unit 27 and the second direction D2 in which the opening 28*a* of the treatment instrument channel 23 opens are arranged in the first space. As shown in FIG. 3, the observation window 34 of the image pickup unit 27 and the opening 28*a* are disposed in the first space.

The suction channel 24 is disposed in the second space, the third space, or the fourth space that is different from the first space. In this case, the suction channel 24 disposed in the second space includes the opening 24*a* in the second space or the third space. In a case where the suction channel 24 is disposed in the third space, the opening 24*a* is included in the second space, the third space, or the fourth space. In a case where the suction channel 24 is disposed in the fourth space, the opening 24*a* is included in the third space or the fourth space. Note that the opening 24*a* may be provided at the most distal end of the distal end structural portion 10*a*, that is, in the longitudinal axis direction of the insertion portion 10. The relations among the above-described first space, second space, third space, fourth space, first direction D1, second direction D2, and third direction D3 can be depicted as in FIG. 5. In other words, it can be said that in the circumferential direction of the longitudinal axis, the second direction is arranged between the first direction and the third direction. The arrangement can be also rephrased as the third direction being arranged between the first direction and the second direction in the circumferential direction.

The number of the suction channels 24 is not limited to one, but a plurality of suction channels 24 may be disposed. In other words, the endoscope 1 may include any two or all of the three suction channels 24 shown in FIG. 5. In a case where a plurality of suction channels 24 are disposed as such, the plurality of suction channels 24 are merged into one in a position of the suction port 11*e* or on the distal end side relative to the suction port 11*e* and are connected to one suction port 11*e*.

In this manner, in the endoscope 1, the treatment instrument channel 23 and the suction channel 24 are independently provided. In the endoscope 1, the opening 24*a* of the suction channel 24 is provided so as to open in a direction different from the opening 28*a* of the treatment instrument channel 23.

As a result, body fluid or the like is drawn into the suction channel 24 provided separately from the treatment instrument channel 23. Thus, the endoscope 1 can reduce the risk of adhesion of body fluid or the like to the treatment instrument when the treatment instrument is inserted into the treatment instrument channel 23.

Accordingly, according to the endoscope of the present embodiment, the risk of adhesion of bacteria to the treatment instrument inserted into the treatment instrument insertion channel can be reduced.

Second Embodiment

Next, a second embodiment will be described.

Figure 6:
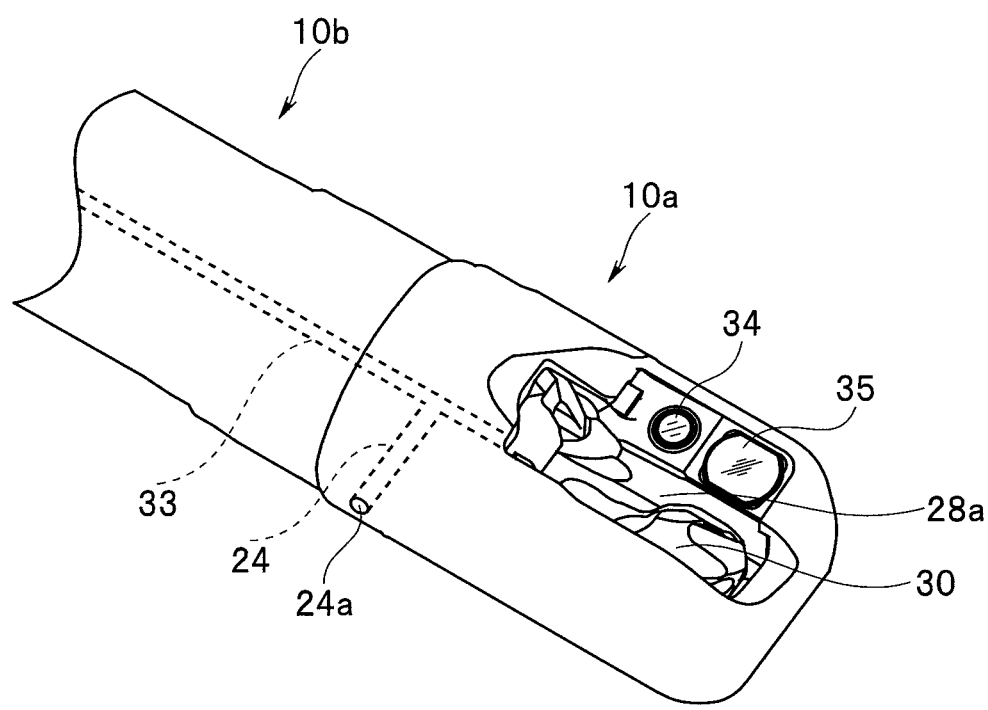
FIG. 6 is a perspective view showing the configuration of the distal end of the insertion portion of the endoscope according to a second embodiment.

FIG. 6 is a perspective view showing the configuration of the distal end of the insertion portion of the endoscope according to the second embodiment. Note that in FIG. 6, the same components as the components of FIG. 1 to FIG. 3 are assigned the same reference numerals and the descriptions will be omitted.

As shown in FIG. 6, in the endoscope 1 of the second embodiment, the opening 24*a* is provided on a side surface that is different from the side surface where the opening 28*a* of the treatment instrument channel 23 of the distal end structural portion 10*a* is provided, specifically, on a side surface on the left side when the distal end structural portion 10*a* is viewed from the distal end side. The opening 24*a* of the suction channel 24 is provided on the proximal end side relative to the opening 28*a* of the treatment instrument channel 23 and the optical axis of the image pickup unit 27. Note that the opening 24*a* may be provided on another side surface as long as the side surface is different from the side surface where the opening 28*a* is provided, without limiting to the arrangement of FIG. 6.

The distal end structural portion 10*a* includes the suction channel 24 in the radial direction of the distal end structural portion 10*a*. One end of the suction channel 24 communicates with the opening 24*a* and the other end communicates with the raising wire channel 33. In other words, the endoscope 1 of the present embodiment uses the raising wire channel 33 communicating with the suction channel 24 as a conduit for suction.

In this manner, in the endoscope 1, the suction channel 24 communicates with the raising wire channel 33 so as to be provided separately from the treatment instrument channel 23. Further, in the endoscope 1, the opening 24*a* of the suction channel 24 is provided so as to open in a direction different from the opening 28*a* of the treatment instrument channel 23.

As a result, body fluid or the like is drawn into the suction channel 24 that is separate from the treatment instrument channel 23, and the raising wire channel 33. Thus, the endoscope 1 can reduce the risk of adhesion of body fluid or the like to the treatment instrument when the treatment instrument is inserted into the treatment instrument channel 23.

Accordingly, according to the endoscope of the second embodiment, similarly to the first embodiment, the risk of adhesion of bacteria to the treatment instrument inserted into the treatment instrument insertion channel can be reduced.

Third Embodiment

Next, a third embodiment will be described.

Figure 7:
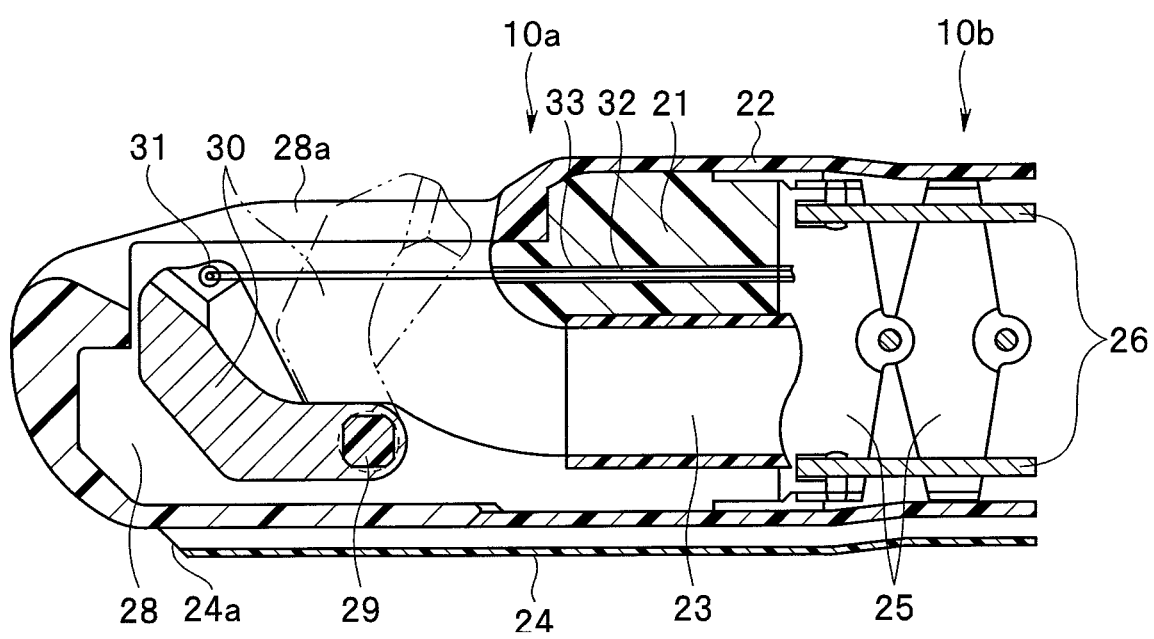
FIG. 7 is a cross-sectional view showing the configuration of the distal end of the insertion portion of the endoscope according to a third embodiment.

FIG. 7 is a cross-sectional view showing the configuration of the distal end of the insertion portion of the endoscope according to the third embodiment. Note that in FIG. 7, the same components as the components of FIG. 1 and FIG. 2 are assigned the same reference numerals and the descriptions will be omitted.

As shown in FIG. 7, in the endoscope 1 of the present embodiment, the suction channel 24 formed by a tube is externally fitted to the insertion portion 10. In other words, the suction channel 24 is externally attached to the insertion portion 10.

The suction channel 24 includes the opening 24a that opens in a direction different from the opening 28a of the treatment instrument channel 23, specifically, in the longitudinal axis direction of the insertion portion 10.

In this manner, in the endoscope 1, the suction channel 24 is externally fitted to the insertion portion 10 so as to be provided separately from the treatment instrument channel 23 and the opening 24a is provided so as to open in a direction different from the opening 28a. The opening 24a is disposed in the fourth space described in the first embodiment, and the observation window 34 and the opening 28a are disposed in the first space.

As a result, body fluid or the like is drawn into the suction channel 24 that is separate from the treatment instrument channel 23. Thus, the endoscope 1 can reduce the risk of adhesion of body fluid or the like to the treatment instrument when the treatment instrument is inserted into the treatment instrument channel 23.

Accordingly, according to the endoscope of the third embodiment, similarly to the first embodiment, the risk of adhesion of bacteria to the treatment instrument inserted into the treatment instrument insertion channel can be reduced.

The present disclosure is not limited to the aforementioned embodiments, but may be changed, modified, or the like in various manners within the scope in which the gist of the present disclosure is not changed.

What is claimed is:

1. An endoscope, comprising:

an insertion portion including a distal end structure and an active bending section;

an image sensor located in the distal end structure;

a housing chamber located in the distal end structure and including an opening on a side surface of the distal end structure;

a treatment instrument channel located in the distal end structure and adjacent the image sensor, wherein a distal end opening of the treatment instrument channel is in communication with the opening of the housing chamber; and a suction channel located in the distal end structure, wherein, in a view along a central longitudinal axis of the distal end structure from a distal end to a proximal end, a first imaginary diameter divides the distal end structure into an upper half portion and a lower half portion and a second imaginary diameter intersects the first imaginary diameter at 90 degrees and divides the upper half portion into a first quadrant and a second quadrant and divides the lower half portion into a third quadrant and a fourth quadrant, wherein each of the first quadrant, the second quadrant, the third quadrant, and the fourth quadrant includes a circumferential portion of a wall of the distal end structure and a portion of an interior space of the distal end structure, wherein the opening of the housing chamber and an observation window of the image sensor are located in the first quadrant, wherein the distal end opening of the suction channel is located in the circumferential portion of at least one of the second quadrant, the third quadrant, and the fourth quadrant, wherein an optical axis of the observation window of the image sensor extends in a first direction, wherein an axis of the opening of the housing chamber extends in a second direction, wherein an axis of the distal end opening of the suction channel extends in a third direction, and wherein in a circumferential direction relative to the central longitudinal axis, the second direction is between the first direction and the third direction.

2. The endoscope according to claim 1, further comprising:

an operation unit located in a proximal end side of the insertion portion;

a treatment instrument insertion opening located in the operation unit and with which a proximal end of the treatment instrument channel communicates; and a suction port located in the operation unit in a position different from the treatment instrument insertion opening and with which a proximal end of the suction channel communicates.

3. The endoscope according to claim 2, wherein a treatment instrument raising base is located in the housing chamber.

4. The endoscope according to claim 2, wherein, relative to the central longitudinal axis, the distal end opening of the suction channel is located distally to the distal end opening of the treatment instrument channel.

5. The endoscope according to claim 2, wherein, relative to the central longitudinal axis, the distal end opening of the suction channel is located distally to the distal end opening of the treatment instrument channel and to an optical axis of the observation window of the image sensor.

6. The endoscope according to claim 2, wherein, relative to the central longitudinal axis, the distal end opening of the suction channel is located proximally to the distal end opening of the treatment instrument channel and to an optical axis of the image sensor.

7. The endoscope according to claim 2, wherein the treatment instrument insertion opening is on a first surface of the operation unit, wherein the suction port is on a second surface of the operation unit, wherein the first surface faces in a first facing direction and the second surface faces in a second facing direction, and wherein the first facing direction is different from the second facing direction.

8. The endoscope according to claim 2, wherein, relative to the central longitudinal axis, the distal end opening of the suction channel is located proximally to the distal end opening of the treatment instrument channel.

9. The endoscope according to claim 1, wherein the suction channel is a tube external to the distal end structure.

10. The endoscope according to claim 1, further comprising:

an operation unit located in a proximal end side of the insertion portion;

a treatment instrument insertion opening located in the operation unit and with which a proximal end of the treatment instrument channel communicates;

a universal cable that extends from the operation unit and in which an extension end is provided with a connector; and a suction port located in the connector and with which a proximal end of the suction channel communicates, the suction port being configured for connection to a suction device.

11. The endoscope according to claim 1, wherein the opening of the housing chamber and the observation window of the image sensor are located in the upper half portion, and wherein the distal end opening of the suction channel is located in the lower half portion.

12. The endoscope according to claim 1, wherein, in the circumferential direction, the second direction is closer to the first direction than to the third direction.

13. The endoscope according to claim 1, wherein the suction channel is separate from the treatment instrument channel.

* * * * *